(12) United States Patent
Sayadi et al.

(10) Patent No.: US 12,336,841 B2
(45) Date of Patent: *Jun. 24, 2025

(54) SPEECH-CONTROLLED HEALTH MONITORING SYSTEMS

(71) Applicant: Sleep Number Corporation, Minneapolis, MN (US)

(72) Inventors: Omid Sayadi, San Jose, CA (US); Steven Jay Young, Los Gatos, CA (US); Carl Hewitt, San Jose, CA (US); Alan Luckow, Ben Lomond, CA (US)

(73) Assignee: Sleep Number Corporation, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/422,371

(22) Filed: Jan. 25, 2024

(65) Prior Publication Data
US 2024/0324951 A1    Oct. 3, 2024

Related U.S. Application Data

(63) Continuation of application No. 17/112,177, filed on Dec. 4, 2020, now Pat. No. 11,931,168.
(Continued)

(51) Int. Cl.
*A61B 5/00*  (2006.01)
*A61B 5/0205* (2006.01)
(Continued)

(52) U.S. Cl.
CPC .......... *A61B 5/4818* (2013.01); *A61B 5/0022* (2013.01); *A61B 5/0205* (2013.01);
(Continued)

(58) Field of Classification Search
CPC ... A61B 5/4818; A61B 5/0022; A61B 5/0205; A61B 5/0823; A61B 5/11; A61B 5/4842;
(Continued)

(56) References Cited

U.S. PATENT DOCUMENTS

| 4,766,628 A | 8/1988 | Greer et al. |
| 4,788,729 A | 12/1988 | Greer et al. |

(Continued)

FOREIGN PATENT DOCUMENTS

| CA | 2346207 | 5/2000 |
| CN | 2352936 | 12/1999 |

(Continued)

OTHER PUBLICATIONS

MayoClinic.com [online], "Alzheimer's Disease," 2024, retrieved from URL<https://www.mayoclinic.org/diseases-conditions/alzheimers-disease/symptoms-causes/syc-20350447>, 17 pages.
(Continued)

*Primary Examiner* — Lynsey C Eiseman
*Assistant Examiner* — Amanda L Steinberg
(74) *Attorney, Agent, or Firm* — Fish & Richardson P.C.

(57) ABSTRACT

Systems and methods for speech-controlled or speech-enabled health monitoring of a subject are described. A device includes a substrate configured to support a subject, a plurality of non-contact sensors configured to capture acoustic signals and force signals with respect to the subject, an audio interface configured to communicate with the subject, and a processor in connection with the plurality of sensors and the audio interface. The processor configured to determine biosignals from one or more of the acoustic signals and the force signals to monitor a subject's health status, and detect presence of speech in the acoustic signals. The audio interface configured to interactively communicate with at least one of the subject or an entity associated with the subject based on at least one of an action needed due to the subject's health status and a verbal command in detected speech.

18 Claims, 8 Drawing Sheets

Related U.S. Application Data

(60) Provisional application No. 63/003,551, filed on Apr. 1, 2020.

(51) Int. Cl.
   *A61B 5/024* (2006.01)
   *A61B 5/08* (2006.01)
   *A61B 5/11* (2006.01)
   *G06F 21/60* (2013.01)
   *G10L 15/18* (2013.01)
   *G10L 15/22* (2006.01)
   *G10L 25/66* (2013.01)
   *G10L 25/78* (2013.01)
   *G16H 40/67* (2018.01)

(52) U.S. Cl.
   CPC .............. *A61B 5/0823* (2013.01); *A61B 5/11* (2013.01); *A61B 5/4842* (2013.01); *A61B 5/6887* (2013.01); *A61B 5/7405* (2013.01); *A61B 5/746* (2013.01); *A61B 5/747* (2013.01); *A61B 5/749* (2013.01); *G06F 21/602* (2013.01); *G10L 15/1815* (2013.01); *G10L 15/22* (2013.01); *G10L 25/66* (2013.01); *G10L 25/78* (2013.01); *G16H 40/67* (2018.01); *A61B 5/024* (2013.01); *A61B 5/0816* (2013.01); *A61B 5/7203* (2013.01); *A61B 5/7267* (2013.01); *A61B 2562/0204* (2013.01); *A61B 2562/0219* (2013.01); *A61B 2562/0247* (2013.01); *G10L 2015/223* (2013.01)

(58) Field of Classification Search
   CPC ..... A61B 5/6887; A61B 5/7405; A61B 5/746; A61B 5/747; A61B 5/749; A61B 5/024; A61B 5/0816; A61B 5/7203; A61B 5/7267; A61B 2562/0204; A61B 2562/0219; A61B 2562/0247; G16H 40/67; G06F 21/602; G10L 15/1815; G10L 15/22; G10L 25/66; G10L 25/78; G10L 2015/223
   See application file for complete search history.

(56) References Cited

U.S. PATENT DOCUMENTS

| | | |
|---|---|---|
| D300,194 S | 3/1989 | Walker |
| 4,829,616 A | 5/1989 | Walker |
| 4,890,344 A | 1/1990 | Walker |
| 4,897,890 A | 2/1990 | Walker |
| 4,908,895 A | 3/1990 | Walker |
| D313,973 S | 1/1991 | Walker |
| 4,991,244 A | 2/1991 | Walker |
| 5,144,706 A | 9/1992 | Walker et al. |
| 5,170,522 A | 12/1992 | Walker |
| 5,430,266 A | 7/1995 | Austin, Jr. et al. |
| D368,475 S | 4/1996 | Scott |
| 5,509,154 A | 4/1996 | Shafer et al. |
| 5,564,140 A | 10/1996 | Shoenhair et al. |
| 5,642,546 A | 6/1997 | Shoenhair |
| 5,652,484 A | 7/1997 | Shafer et al. |
| 5,765,246 A | 6/1998 | Shoenhair |
| 5,903,941 A | 5/1999 | Shafer et al. |
| 5,904,172 A | 5/1999 | Gifft et al. |
| 6,037,723 A | 3/2000 | Shafer et al. |
| 6,108,844 A | 8/2000 | Kraft et al. |
| 6,161,231 A | 12/2000 | Kraft et al. |
| 6,202,239 B1 | 3/2001 | Ward et al. |
| 6,397,419 B1 | 6/2002 | Mechache |
| 6,483,264 B1 | 11/2002 | Shafer et al. |
| 6,686,711 B2 | 2/2004 | Rose et al. |
| 6,708,357 B2 | 3/2004 | Gaboury et al. |
| 6,763,541 B2 | 7/2004 | Mahoney et al. |
| 6,804,848 B1 | 10/2004 | Rose |
| 6,832,397 B2 | 12/2004 | Gaboury |
| D502,929 S | 3/2005 | Copeland et al. |
| 6,883,191 B2 | 5/2005 | Gaboury et al. |
| 7,107,095 B2 | 7/2006 | Manolas |
| 7,343,197 B2 | 3/2008 | Shusterman |
| 7,389,554 B1 | 6/2008 | Rose |
| 7,666,151 B2 | 2/2010 | Sullivan et al. |
| D611,498 S | 3/2010 | Alvarez |
| D611,499 S | 3/2010 | Alvarez |
| 7,865,988 B2 | 1/2011 | Koughan et al. |
| D640,280 S | 6/2011 | Davis et al. |
| D669,499 S | 10/2012 | Gardner et al. |
| 8,287,452 B2 | 10/2012 | Rifredi et al. |
| 8,336,369 B2 | 12/2012 | Mahoney |
| D674,400 S | 1/2013 | Fong et al. |
| D678,312 S | 3/2013 | Christie et al. |
| 8,444,558 B2 | 5/2013 | Young et al. |
| D690,723 S | 10/2013 | Steele et al. |
| D691,118 S | 10/2013 | Ingham et al. |
| D696,268 S | 12/2013 | Hyunjung et al. |
| D696,271 S | 12/2013 | Lee et al. |
| D696,677 S | 12/2013 | Corcoran et al. |
| D697,874 S | 1/2014 | Stusynski et al. |
| D698,338 S | 1/2014 | Ingham |
| D701,536 S | 3/2014 | Sakal |
| 8,672,842 B2 | 3/2014 | Kenalty et al. |
| 8,672,853 B2 | 3/2014 | Young |
| D709,909 S | 7/2014 | Pasquero et al. |
| 8,769,747 B2 | 7/2014 | Mahoney et al. |
| 8,882,684 B2 | 11/2014 | Halperin |
| 8,892,679 B1 | 11/2014 | Destagnol et al. |
| 8,893,339 B2 | 11/2014 | Fleury |
| D720,762 S | 1/2015 | Seo et al. |
| 8,931,329 B2 | 1/2015 | Mahoney et al. |
| 8,966,689 B2 | 3/2015 | McGuire et al. |
| 8,973,183 B1 | 3/2015 | Palashewski et al. |
| 8,984,687 B2 | 3/2015 | Stusynski et al. |
| 9,005,101 B1 | 4/2015 | Van Erlach |
| D737,250 S | 8/2015 | Ingham et al. |
| 9,131,781 B2 | 9/2015 | Zaiss et al. |
| D743,976 S | 11/2015 | Wilberding et al. |
| D745,884 S | 12/2015 | Shardlow et al. |
| 9,228,885 B2 | 1/2016 | Zerhusen et al. |
| D752,624 S | 3/2016 | Butcher et al. |
| 9,271,665 B2 | 3/2016 | Sarrafzadeh et al. |
| D754,672 S | 4/2016 | Wilberding et al. |
| D755,823 S | 5/2016 | Chen et al. |
| 9,370,457 B2 | 6/2016 | Nunn et al. |
| 9,375,142 B2 | 6/2016 | Schultz et al. |
| D761,293 S | 7/2016 | Wiesner et al. |
| 9,392,879 B2 | 7/2016 | Nunn et al. |
| D762,716 S | 8/2016 | Yang et al. |
| 9,445,751 B2 | 9/2016 | Young et al. |
| D771,123 S | 11/2016 | Anzures et al. |
| D772,905 S | 11/2016 | Ingenlath |
| 9,504,416 B2 | 11/2016 | Young et al. |
| D774,071 S | 12/2016 | Parker et al. |
| 9,510,688 B2 | 12/2016 | Nunn et al. |
| D775,631 S | 1/2017 | Lee |
| D778,301 S | 2/2017 | Toda |
| 9,592,005 B2 | 3/2017 | Oakhill |
| D785,003 S | 4/2017 | Yun et al. |
| D785,660 S | 5/2017 | Kim et al. |
| D787,533 S | 5/2017 | Butcher et al. |
| D787,551 S | 5/2017 | Oh et al. |
| 9,635,953 B2 | 5/2017 | Nunn et al. |
| D789,391 S | 6/2017 | Cabrera et al. |
| D789,956 S | 6/2017 | Ortega et al. |
| D792,908 S | 7/2017 | Barajas et al. |
| 9,730,524 B2 | 8/2017 | Chen et al. |
| 9,737,154 B2 | 8/2017 | Mahoney et al. |
| 9,770,114 B2 | 9/2017 | Brosnan et al. |
| D799,518 S | 10/2017 | Wilson et al. |
| D800,140 S | 10/2017 | Lee et al. |
| D800,162 S | 10/2017 | Havranek |
| D800,778 S | 10/2017 | Oh et al. |
| 9,844,275 B2 | 12/2017 | Nunn et al. |
| D809,843 S | 2/2018 | Keeley et al. |

(56) References Cited

U.S. PATENT DOCUMENTS

| | | |
|---|---|---|
| D812,393 S | 3/2018 | Karschnik et al. |
| 9,924,813 B1 | 3/2018 | Basten et al. |
| 9,931,085 B2 | 4/2018 | Young et al. |
| D822,708 S | 7/2018 | Ghosh |
| 10,058,467 B2 | 8/2018 | Stusynski et al. |
| 10,092,242 B2 | 10/2018 | Nunn et al. |
| D834,593 S | 11/2018 | Lehmann et al. |
| 10,143,312 B2 | 12/2018 | Brosnan et al. |
| 10,149,549 B2 | 12/2018 | Erko et al. |
| 10,182,661 B2 | 1/2019 | Nunn et al. |
| D840,428 S | 2/2019 | Narinedhat et al. |
| 10,194,752 B2 | 2/2019 | Zaiss et al. |
| 10,194,753 B2 | 2/2019 | Fleury et al. |
| 10,201,234 B2 | 2/2019 | Nunn et al. |
| 10,251,490 B2 | 4/2019 | Nunn et al. |
| 10,314,407 B1 | 6/2019 | Main et al. |
| 10,342,358 B1 | 7/2019 | Palashewski et al. |
| 10,360,368 B2 | 7/2019 | Berman et al. |
| D855,643 S | 8/2019 | Schwer et al. |
| 10,448,749 B2 | 10/2019 | Palashewski et al. |
| 10,555,850 B2 | 2/2020 | Meyer et al. |
| D890,792 S | 7/2020 | Valladares et al. |
| 10,729,253 B1 | 8/2020 | Gaunt |
| D896,266 S | 9/2020 | Kennedy et al. |
| D902,244 S | 11/2020 | Kim et al. |
| D903,700 S | 12/2020 | Valladares et al. |
| D916,745 S | 5/2021 | Stusynski et al. |
| 11,001,447 B2 | 5/2021 | Shutes et al. |
| D932,808 S | 10/2021 | Keeley |
| D954,725 S | 6/2022 | Stusynski et al. |
| 11,376,178 B2 | 7/2022 | Demirli et al. |
| 11,399,636 B2 | 8/2022 | Demirli et al. |
| 11,424,646 B2 | 8/2022 | Holmvik et al. |
| D968,436 S | 11/2022 | Stusynski et al. |
| D975,121 S | 1/2023 | Stusynski et al. |
| 11,670,404 B2 | 6/2023 | Sayadi et al. |
| 2003/0052787 A1 | 3/2003 | Zerhusen et al. |
| 2006/0116589 A1 | 6/2006 | Park |
| 2007/0157385 A1 | 7/2007 | Lemire et al. |
| 2007/0164871 A1 | 7/2007 | Dionne et al. |
| 2008/0005843 A1 | 1/2008 | Lokhorst et al. |
| 2008/0077020 A1 | 3/2008 | Young et al. |
| 2008/0120784 A1 | 5/2008 | Warner et al. |
| 2008/0122616 A1 | 5/2008 | Warner et al. |
| 2008/0126122 A1 | 5/2008 | Warner et al. |
| 2008/0146890 A1 | 6/2008 | LeBoeuf et al. |
| 2008/0235872 A1 | 10/2008 | Newkirk et al. |
| 2009/0177495 A1 | 7/2009 | Abousy et al. |
| 2010/0170043 A1 | 7/2010 | Young et al. |
| 2011/0144455 A1 | 6/2011 | Young et al. |
| 2011/0224510 A1 | 9/2011 | Oakhill |
| 2011/0265003 A1 | 10/2011 | Schubert et al. |
| 2012/0089419 A1 | 4/2012 | Huster et al. |
| 2012/0265024 A1 | 10/2012 | Shrivastav et al. |
| 2013/0267791 A1 | 10/2013 | Halperin |
| 2013/0332318 A1 | 12/2013 | D'Auria et al. |
| 2013/0340168 A1 | 12/2013 | Meyer et al. |
| 2014/0026322 A1 | 1/2014 | Bell et al. |
| 2014/0066798 A1 | 3/2014 | Albert |
| 2014/0250597 A1 | 9/2014 | Chen et al. |
| 2014/0259418 A1 | 9/2014 | Nunn et al. |
| 2014/0277822 A1 | 9/2014 | Nunn et al. |
| 2015/0007393 A1 | 1/2015 | Palashewski |
| 2015/0025327 A1 | 1/2015 | Young et al. |
| 2015/0097682 A1 | 4/2015 | Rossi et al. |
| 2015/0169840 A1 | 6/2015 | Kupfer et al. |
| 2015/0182397 A1 | 7/2015 | Palashewski et al. |
| 2015/0182399 A1 | 7/2015 | Palashewski et al. |
| 2015/0182418 A1 | 7/2015 | Zaiss |
| 2015/0277703 A1 | 10/2015 | Davis |
| 2016/0058337 A1 | 3/2016 | Blahnik et al. |
| 2016/0100696 A1 | 4/2016 | Palashewski et al. |
| 2016/0110986 A1 | 4/2016 | Rosenblood |
| 2016/0151603 A1 | 6/2016 | Shouldice et al. |
| 2016/0242562 A1 | 8/2016 | Karschnik et al. |
| 2016/0338871 A1 | 11/2016 | Nunn et al. |
| 2016/0353996 A1 | 12/2016 | Fink |
| 2016/0367039 A1 | 12/2016 | Young et al. |
| 2017/0003666 A1 | 1/2017 | Nunn et al. |
| 2017/0049243 A1 | 2/2017 | Nunn et al. |
| 2017/0055896 A1 | 3/2017 | Al-Ali et al. |
| 2017/0095196 A1 | 4/2017 | Oakhill |
| 2017/0191516 A1 | 7/2017 | Griffith et al. |
| 2017/0203157 A1 | 7/2017 | Volkerink et al. |
| 2017/0231545 A1 | 8/2017 | Shinar et al. |
| 2017/0255751 A1 | 9/2017 | Sanmugalingha |
| 2017/0281054 A1 | 10/2017 | Stever |
| 2017/0303697 A1 | 10/2017 | Chen et al. |
| 2017/0318980 A1 | 11/2017 | Mahoney et al. |
| 2017/0354268 A1 | 12/2017 | Brosnan et al. |
| 2017/0374186 A1 | 12/2017 | Velusamy et al. |
| 2018/0106897 A1 | 4/2018 | Shouldice |
| 2018/0116415 A1 | 5/2018 | Karschnik et al. |
| 2018/0116418 A1 | 5/2018 | Shakal et al. |
| 2018/0116419 A1 | 5/2018 | Shakal et al. |
| 2018/0116420 A1 | 5/2018 | Shakal |
| 2018/0119686 A1 | 5/2018 | Shakal et al. |
| 2018/0125259 A1 | 5/2018 | Peterson et al. |
| 2018/0125260 A1 | 5/2018 | Peterson et al. |
| 2018/0184920 A1 | 7/2018 | Rabinovich et al. |
| 2018/0341448 A1 | 11/2018 | Behzadi et al. |
| 2018/0353085 A1 | 12/2018 | Olivero |
| 2019/0029597 A1 | 1/2019 | Nunn et al. |
| 2019/0059603 A1 | 2/2019 | Griffith et al. |
| 2019/0082855 A1 | 3/2019 | Brosnan et al. |
| 2019/0104858 A1 | 4/2019 | Erko et al. |
| 2019/0125095 A1 | 5/2019 | Nunn et al. |
| 2019/0125097 A1 | 5/2019 | Nunn et al. |
| 2019/0200777 A1 | 7/2019 | Demirli et al. |
| 2019/0201265 A1 | 7/2019 | Sayadi et al. |
| 2019/0201266 A1 | 7/2019 | Sayadi et al. |
| 2019/0201267 A1 | 7/2019 | Demirli et al. |
| 2019/0201268 A1 | 7/2019 | Sayadi et al. |
| 2019/0201269 A1 | 7/2019 | Sayadi et al. |
| 2019/0201270 A1 | 7/2019 | Sayadi et al. |
| 2019/0201271 A1 | 7/2019 | Grey et al. |
| 2019/0206416 A1 | 7/2019 | Demirli et al. |
| 2019/0209405 A1 | 7/2019 | Sayadi et al. |
| 2019/0220511 A1 | 7/2019 | Zheng et al. |
| 2019/0279745 A1 | 9/2019 | Sayadi et al. |
| 2019/0282178 A1 | 9/2019 | Volosin |
| 2019/0328146 A1 | 10/2019 | Palashewski et al. |
| 2019/0328147 A1 | 10/2019 | Palashewski et al. |
| 2019/0336367 A1 | 11/2019 | Zerhusen et al. |
| 2020/0075136 A1 | 3/2020 | Harper et al. |
| 2020/0110194 A1 | 4/2020 | Young et al. |
| 2020/0146910 A1 | 5/2020 | Demirli et al. |
| 2020/0163627 A1 | 5/2020 | Sayadi et al. |
| 2020/0202120 A1 | 6/2020 | Shelly |
| 2020/0205580 A1 | 7/2020 | Sayadi et al. |
| 2020/0227160 A1 | 7/2020 | Youngblood |
| 2020/0337470 A1 | 10/2020 | Sayadi et al. |
| 2020/0405240 A1 | 12/2020 | Palashewski et al. |
| 2021/0022667 A1 | 1/2021 | Siyahjani et al. |
| 2021/0150873 A1 | 5/2021 | Shouldice |
| 2021/0307683 A1 | 10/2021 | Sayadi et al. |
| 2022/0007965 A1 | 1/2022 | Tiron et al. |
| 2022/0087607 A1 | 3/2022 | Ganesan |
| 2022/0133164 A1 | 5/2022 | Mushtaq et al. |
| 2022/0175600 A1 | 6/2022 | Molina et al. |
| 2022/0265223 A1 | 8/2022 | Molina |
| 2022/0323001 A1 | 10/2022 | Nunn et al. |
| 2023/0046169 A1 | 2/2023 | Molina et al. |
| 2023/0115150 A1 | 4/2023 | Demirli et al. |
| 2023/0190183 A1 | 6/2023 | Molina et al. |
| 2023/0218225 A1 | 7/2023 | Mushtaq et al. |
| 2023/0225517 A1 | 7/2023 | Sayadi et al. |
| 2023/0240922 A1 | 8/2023 | Rao et al. |
| 2023/0329583 A1 | 10/2023 | Molina et al. |
| 2023/0335239 A1 | 10/2023 | Sayadi et al. |
| 2023/0414178 A1 | 12/2023 | Molina et al. |
| 2024/0032860 A1 | 2/2024 | Rao et al. |
| 2024/0032861 A1 | 2/2024 | Stusynski et al. |
| 2024/0060815 A1 | 2/2024 | Young et al. |

(56) References Cited

U.S. PATENT DOCUMENTS

| | | |
|---|---|---|
| 2024/0065559 A1 | 2/2024 | Molina et al. |
| 2024/0082532 A1 | 3/2024 | Barr et al. |
| 2024/0115192 A1 | 4/2024 | Sayadi et al. |

FOREIGN PATENT DOCUMENTS

| | | |
|---|---|---|
| CN | 101201273 | 6/2008 |
| CN | 103381123 | 11/2013 |
| CN | 104822355 | 8/2015 |
| CN | 105877712 | 8/2016 |
| CN | 207837242 | 9/2018 |
| CN | 108697241 | 10/2018 |
| CN | 108784127 | 11/2018 |
| CN | 110250785 A | 9/2019 |
| EP | 1180352 | 2/2002 |
| JP | 2001-037729 | 2/2001 |
| JP | 2001-178834 | 7/2001 |
| JP | 2001-252253 | 9/2001 |
| JP | 2007-135863 | 6/2007 |
| JP | 2010-160783 | 7/2010 |
| JP | 2009-541010 A5 | 7/2011 |
| JP | 2013-215252 | 10/2013 |
| JP | 2013-541973 A | 11/2013 |
| JP | 2016-518159 | 6/2016 |
| JP | 2017-510390 | 4/2017 |
| JP | 2017-535316 A | 11/2017 |
| JP | 2018-511363 A | 4/2018 |
| WO | WO 2000/004828 | 2/2000 |
| WO | WO 2016/170005 | 10/2016 |
| WO | WO 2017/032873 | 3/2017 |
| WO | WO 2017/068581 | 4/2017 |
| WO | WO 2017/122178 | 6/2017 |
| WO | WO 2019/081915 | 5/2019 |
| WO | 10-2080534 | 2/2020 |

OTHER PUBLICATIONS

MayoClinic.com [online], "Breast Cancer," 2024, retrieved from URL<https://www.mayoclinic.org/diseases-conditions/breast-cancer/diagnosis-treatment/drc-20352475>, 15 pages.

MayoClinic.com [online], "Diabetes," 2024, retrieved from URL<https://www.mayoclinic.org/diseases-conditions/diabetes/symptoms-causes/syc-20371444>, 12 pages.

U.S. Appl. No. 18/094,751, filed Jan. 9, 2023, Sayadi et al.

U.S. Appl. No. 18/398,611, filed Dec. 18, 2023, Sayadi et al.

U.S. Appl. No. 18/417,870, filed Jan. 19, 2024, Demirli et al.

U.S. Appl. No. 18/437,909, filed Feb. 9, 2024, Mushtaq et al.

U.S. Appl. No. 18/584,517, filed Feb. 22, 2024, Garcia Molina et al.

U.S. Appl. No. 62/742,613, filed Oct. 8, 2018, Young et al.

U.S. Appl. No. 62/804,623, filed Feb. 12, 2019, Young et al.

U.S. Appl. No. 63/003,551, filed Apr. 1, 2020, Young et al.

[No Author Listed] [online], "Leesa vs. Casper Mattress Review—Best Memory Foam Mattress", Mar. 2019, retrieved on Dec. 10, 2020, retrieved from URL<https://webarchive.org/web/20190304041833/https//www.rizknows.com/buyerguides/leesa-vs-casper-mattress-review-best-memory-foam-mattress/>, 1 page.

Alves, "iPhone App Registration Flow," Dribbble, published Oct. 23, 2014, retrieved from the Internet Jan. 26, 2022, Internet URL<https://dribbble.com/shots/1778356-iPhone-App-Registration-Flow>, 3 pages.

Extended European Search Report in European Appln No. 20928266.4, dated Mar. 19, 2024, 12 pages.

Extended European Search Report in European Appln No. 20929014.7, dated May 7, 2024, 12 pages.

Gold, "Sign Up/Log In modal for iOS app," Dribbble, published May 7, 2013, retrieved from the Internet Jan. 26, 2022, Internet URL<https://dribbble.com/shots/1061991-Sign-Up-Log-In-modal-for-iOS-app>, 3 pages.

International Search Report and Written Opinion in International Appln. No. PCT/US2020/063329, mailed on Apr. 5, 2021, 11 pages.

International Search Report and Written Opinion in International Appln. No. PCT/US2020/063338, mailed on Mar. 30, 2021, 11 pages.

Johns, "Sign Up," Dribbble, published Aug. 2, 2013, retrieved from the Internet Jan. 26, 2022, Internet URL: <https://dribbble.com/shots/1181529-Sign-Up>, 3 pages.

Matus, [online], "The Composition Sketch", Dribble, Sep. 2017, retrieved on Dec. 10, 2020, retrieved from URL: <https://dribbble.com/shots/3821915-The-Composition-Sketch>, 2 pages.

Zaytsev, "Finance iPhone App [Another Direction]," Dribbble, published Jul. 21, 2014, retrieved from the Internet Jan. 26, 2022, Internet URL<https://dribbble.com/shots/1650374-Finance-iPhone-App-Another-Direction>, 3 pages.

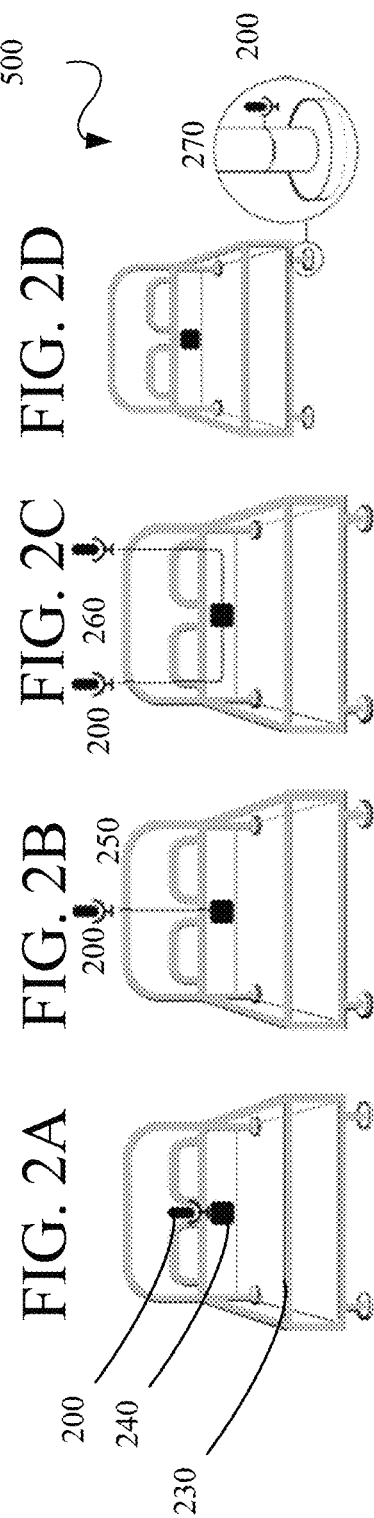
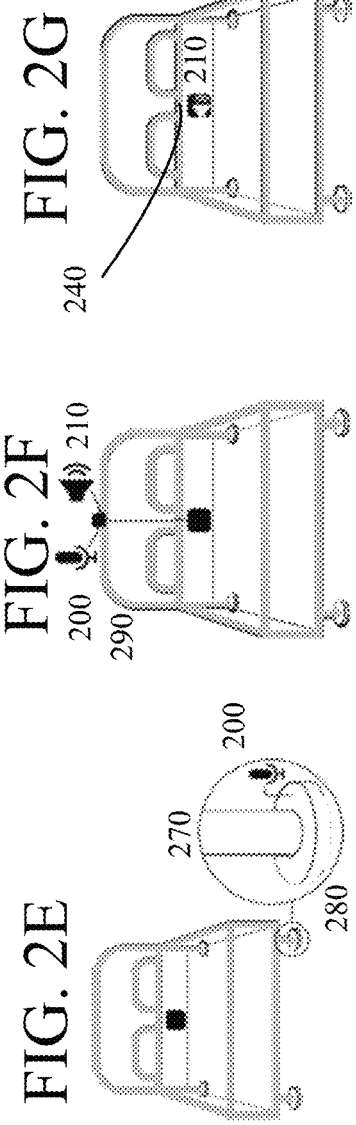
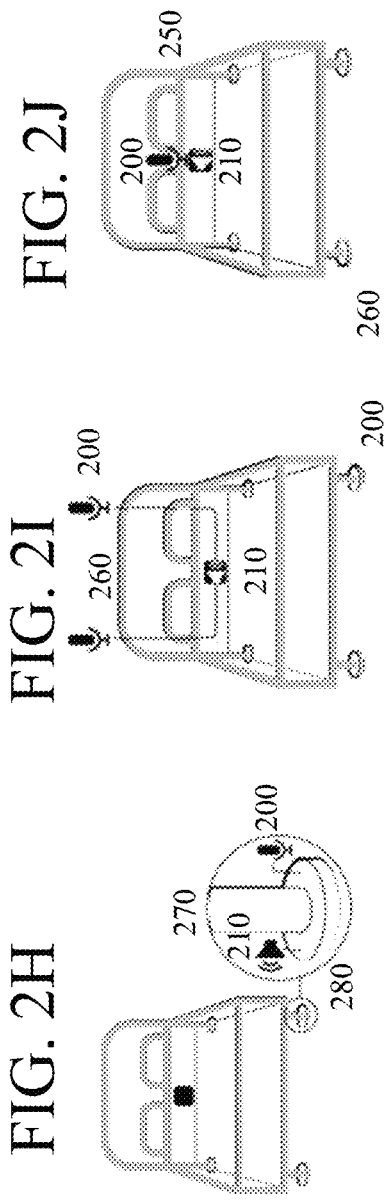

SPEECH-CONTROLLED HEALTH MONITORING SYSTEMS

CROSS-REFERENCE TO RELATED APPLICATIONS

This application is a continuation application of U.S. application Ser. No. 17/112,177, filed Dec. 4, 2020, which claims priority to and the benefit of U.S. Provisional Application Ser. No. 63/003,551, filed Apr. 1, 2020, the entire disclosure of which is hereby incorporated by reference.

TECHNICAL FIELD

This disclosure relates to systems and methods for health monitoring of a subject.

BACKGROUND

Speech enabled technology has become a standard method of interaction with consumer electronic devices for its convenience and simple accessibility, enabling more efficient and faster operations. The medical applications of speech technology has been mostly limited to care checklists, panic calls, and prescription refills. This is mainly due to the fact that these voice enabled devices do not have the ability to directly measure and monitor the physiological parameters of the subject. Unlike persistent conditions, paroxysmal conditions with sudden or intermittent onset require an at home screening solution that can be used immediately and continuously, and need a simple way such as speech to initiate a health check. In addition, many people are bedbound or live with poor health conditions. These people are at risk for falling or experiencing sudden health episodes, such as an apnea, pressure, ulcers, atrial fibrillation, or heart attack. If the person lives alone, there is no one to notice the early warnings, observe the situation, or to call for help.

SUMMARY

Disclosed herein are implementations of systems and methods for speech-controlled or speech-enabled health monitoring of a subject.

In implementations, a device includes a substrate configured to support a subject, a plurality of non-contact sensors configured to capture acoustic signals and force signals with respect to the subject, an audio interface configured to communicate with the subject, and a processor in connection with the plurality of sensors and the audio interface. The processor configured to determine biosignals from one or more of the acoustic signals and the force signals to monitor a subject's health status, and detect presence of speech in the acoustic signals. The audio interface configured to interactively communicate with at least one of the subject or an entity associated with the subject based on at least one of an action needed due to the subject's health status and a verbal command in detected speech.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIGS. 2A-2J are illustrations of sensor placements and configurations.

DETAILED DESCRIPTION

Figure 1:
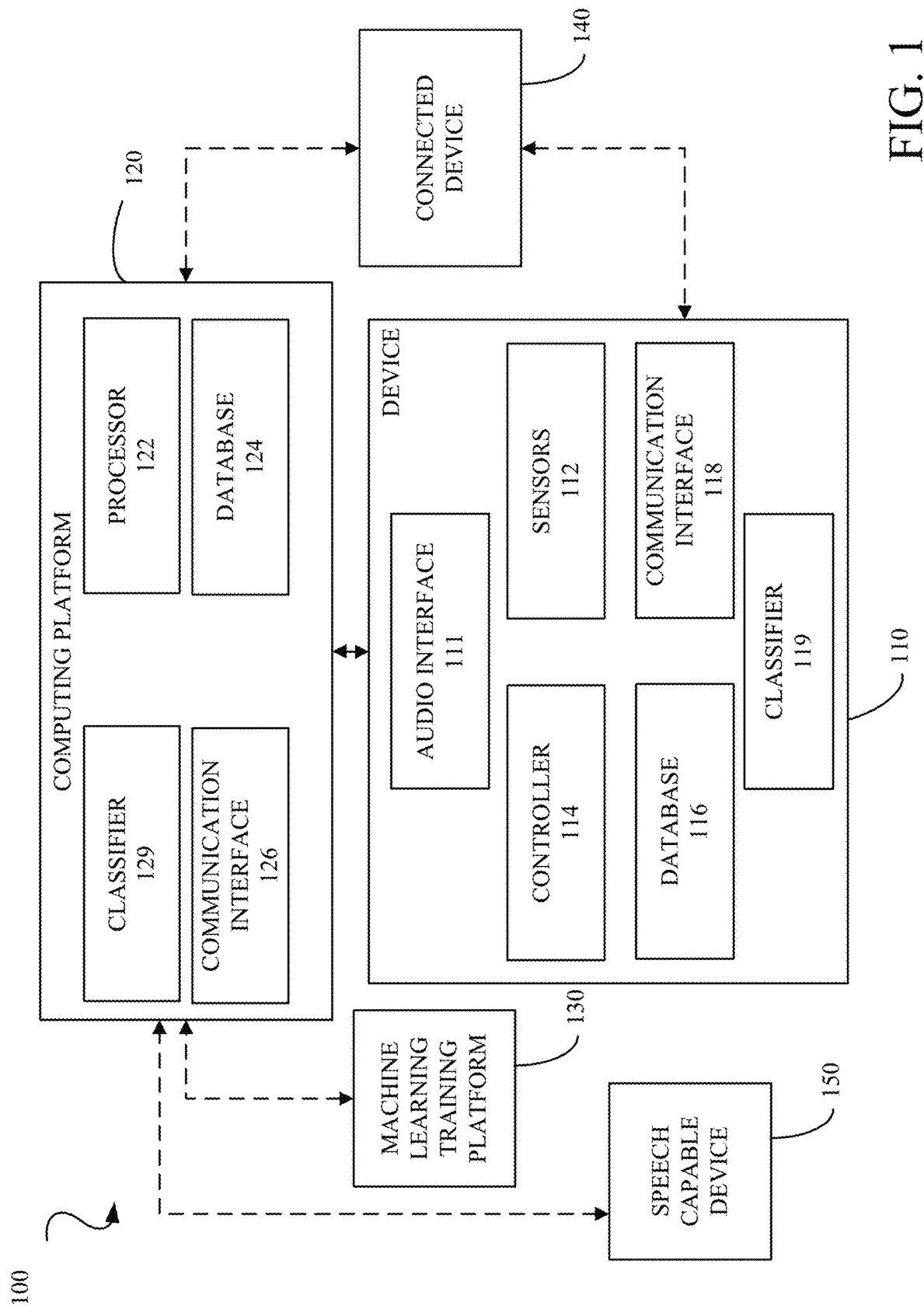
FIG. 1 is a system architecture for a speech-controlled health monitoring system.

Disclosed herein are implementations of systems and methods for speech-controlled or speech-enabled health monitoring of a subject. The systems and methods can be used to passively and continuously monitor the subject's health and verbally interact with the subject to initiate a health check, provide information about the subject's health status, or perform an action such as recording a health related episode or calling emergency services. A subject's health and wellbeing can be monitored using a system that verbally interacts with the subject. Sleep, cardiac, respiration, motion, and sleep disordered breathing monitoring are examples. The subject can use his/her speech to interact with the system to request an action to be performed by the system or to obtain information about the subject's health status. The systems can be used to respond to the commands of a subject's partner in the event the subject is unable or incapacitated.

The systems and methods use one or more non-contact sensors such as audio or acoustic sensors, accelerometers, pressure sensors, load sensors, weight sensors, force sensors, motion sensors, or vibration sensors to capture a sound(s) (speech and disordered breathing) as well as mechanical vibrations of the body (motion and physiological movements of the heart and lungs) and translate that into biosignal information used for screening and identifying health status and disease conditions.

In implementations, the system includes one or more microphones or audio sensors placed near the subject to record acoustic signals, one or more speakers placed near the subject to play back audio, a physiological measurement system that uses one or more non-contact sensors such as accelerometers, pressure sensors, load sensors, weight sensors, force sensors, motion sensors, or vibration sensors to record mechanical vibrations of the body, a speech recognition system, a speech synthesizer, and a processor configured to record the subject's audio and biosignals, process them, detect the subject's speech, process the subject's speech, and initiate a response to the subject's speech. In implementations, the one or more microphones or audio sensors and the one or more non-contact sensors can be placed under, or be built into a substrate, such as a bed, couch, chair, exam table, floor, etc. For example, the one or more microphones or audio sensors and the one or more non-contact sensors can be placed or positioned inside, under, or attached to a control box, legs, bed frame, headboard, or wall. In implementations, the processor can be in the device (control box) or in the computing platform (cloud).

In implementations, the processor is configured to record mechanical force and vibrations of the body, including motion and physiological movements of heart and lungs using one or more non-contact sensors such as accelerometers, pressure sensors, load sensors, weight sensors, force sensors, motion sensors, or vibration sensors. The processor further enhances such data to perform cardiac analysis (including determining heart rate, heartbeat timing, variability, and heartbeat morphology and their corresponding changes from a baseline or range), respiratory analysis (including determining breathing rate, breathing phase, depth, timing and variability, and breathing morphology and their corresponding changes from a baseline or range), and motion analysis (including determining movements amplitude, time, periodicity, and pattern and their corresponding changes from a baseline or range). The processor is configured to record acoustic information, filter unwanted interferences, and enhance it for analytical determinations.

For example, the processor can use the enhanced acoustic information to identify sleep disordered breathing. The processor can then determine a proper response to the detected sleep disordered breathing such as by changing an adjustable feature of the bed (for example, firmness) or bedroom (for example, lighting), or play a sound to make the sleeper change position or transition into a lighter state of sleep and therefore, help stop, reduce, or alter the disordered breathing. For example, the processor can use the enhanced acoustic information to correlate irregular lung or body movements with lung or body sounds. Weezing or other abnormal sounds are an example. For example, the processor can use the enhanced acoustic information to detect if speech has been initiated. The processor compares the audio stream against a dictionary of electronic commands to discard unrelated conversations and to determine if a verbal command to interact with the system has been initiated.

In implementations, the processor is configured to handle speech recognition. For example, the processor can perform speech recognition. This can include detecting a trigger (for example, a preset keyword or phrase) and determining the context. A key word could be, for example, "Afib" to trigger annotating (marking) cardiac recording or generating alerts. For example, the processor can communicate through APIs with other speech capable devices (such as Alexa®, Siri®, and Google®) responsible for recognizing and synthesizing speech.

In implementations, the processor is configured to categorize and initiate a response to the recognized speech. The response can be starting an interactive session with the subject (for example, playing back a tone or playing a synthesized speech) or performing a responsive action (for example, turning on/off a home automation feature, labeling the data with health status markers for future access of the subject or subject's physician, or calling emergency services). The response can also include communicating with other speech capable devices connected to home automation systems or notification systems. The system can also be used to create events based on the analysis, the event may be an audible tone or message sent to the cloud for a critical condition.

The sensors are connected either with a wire, wirelessly or optically to the processor which may be on the internet and running artificial intelligence software. The signals from the sensors can be analyzed locally with a locally present processor or the data can be networked by wire or other means to another computer and remote storage that can process and analyze the real-time and/or historical data. The processor can be a single processor for both mechanical force sensors and audio sensors, or a set of processors to process mechanical force and interact with other speech capable devices. Other sensors such as blood pressure, temperature, blood oxygen and pulse oximetry sensors can be added for enhanced monitoring or health status evaluation. The system can use artificial intelligence and/or machine learning to train classifiers used to process force, audio, and other sensor signals.

In implementations, the speech enabled device can act as a speech recognizer or speech synthesizer to support unidirectional and bidirectional communication with the subject. The speech recognizer uses speech to text, and the speech synthesizer uses text to speech, both based on dictionaries of predefined keywords or phrases. The system includes bidirectional audio (microphone and speakers) to enable two-way communication with the patient (the subject's speech serves as a command, and the device responds upon receiving a command). The system can additionally include interfaces to other voice assistant devices (such as Alexa®, Siri®, and Google®) to process the subject's speech, or to play the synthesized response, or both.

The systems and methods described herein can be used by a subject when experiencing symptoms of a complication or condition or exhibiting the early warning signs of a health related condition, or can be used when instructed by a physician in a telehealth application. For example, the system can be used for in home stress testing where sensors data can be used to monitor indices of heart rate variability to quantify dynamic autonomic modulation or heart rate recovery.

The system can be programmed to limit the number or the individuals who can verbally interact with it. For example, the system may accept and respond to verbal commands only from one person (the subject) or the subject's partner. In such cases, the speech recognition will have voice recognition to only respond to certain individuals. The electronic commands can include, but are not limited to, a verbal request to perform a specific health check on the subject (for example, cardiac check or stress test), give updates about health status of the subject. mark the data when the subject is experiencing a health episode or condition, send a health report to the subject's physician, call emergency services, order a product through API integrations with third parties (for example, purchasing something from an internet seller), and/or interact with adjustable features of home automation. The system can integrate with other means of communication such as a tablet or smartphone to provide video communication.

FIG. 1 is a system architecture for speech-controlled or speech-enabled health monitoring system (SHMS) 100. The SHMS 100 includes one or more devices 110 which are connected to or in communication with (collectively "connected to") a computing platform 120. In implementations, a machine learning training platform 130 may be connected to the computing platform 120. In implementations, a speech capable device 150 may be connected to the computing platform 120 and the one or more devices 110. In implementations, users may access the data via a connected device 140, which may receive data from the computing platform 120, the device 110, the speech capable device 150, or combinations thereof. The connections between the one or more devices 110, the computing platform 120, the machine learning training platform 130, the speech capable device 150, and the connected device 140 can be wired, wireless, optical, combinations thereof and/or the like. The system architecture of the SHMS 100 is illustrative and may include additional, fewer or different devices, entities and the like which may be similarly or differently architected without departing from the scope of the specification and claims herein. Moreover, the illustrated devices may perform other functions without departing from the scope of the specification and claims herein.

In an implementation, the device 110 can include an audio interface 111, one or more sensors 112, a controller 114, a database 116, and a communications interface 118. In an implementation, the device 110 can include a classifier 119 for applicable and appropriate machine learning techniques as described herein. The one or more sensors 112 can detect sound, wave patterns, and/or combinations of sound and wave patterns of vibration, pressure, force, weight, presence, and motion due to subject(s) activity and/or configuration with respect to the one or more sensors 112. In implementations, the one or more sensors 112 can generate more than one data stream. In implementations, the one or sensors 112 can be the same type. In implementations, the one or more sensors 112 can be time synchronized. In implementations, the one or more sensors 112 can measure the partial force of gravity on substrate, furniture or other object. In implementations, the one or more sensors 112 can independently capture multiple external sources of data in one stream (i.e. multivariate signal), for example, weight, heart rate, breathing rate, vibration, and motion from one or more subjects or objects. In an implementation, the data captured by each sensor 112 is correlated with the data captured by at least one, some, all or a combination of the other sensors 112. In implementations, amplitude changes are correlated. In implementations, rate and magnitude of changes are correlated. In implementations, phase and direction of changes are correlated. In implementations, the one or more sensors 112 placement triangulates the location of center of mass. In implementations, the one or more sensors 112 can be placed under or built into the legs of a bed, chair, coach, etc. In implementations, the one or more sensors 112 can be placed under or built into the edges of crib. In implementations, the one or more sensors 112 can be placed under or built into the floor. In implementations, the one or more sensors 112 can be placed under or built into a surface area. In implementations, the one or more sensors 112 locations are used to create a surface map that covers the entire area surrounded by sensors. In implementations, the one or more sensors 112 can measure data from sources that are anywhere within the area surrounded by the one or more sensors 112, which can be directly on top of the one or more sensors 112, near the one or more sensors 112, or distant from the one or more sensors 112. The one or more sensors 112 are not intrusive with respect to the subject(s).

The one or more sensors 112 can include one or more non-contact sensors such as audio, microphone or acoustic sensors to capture the sound (speech and sleep disordered breathing) as well as sensors to measure the partial force of gravity on substrate, furniture or other object including accelerometer, pressure, load, weight, force, motion or vibration as well as mechanical vibrations of the body (motion and physiological movements of heart and lungs).

The audio interface 111 provides a bi-directional audio interface (microphone and speakers) to enable two-way communication with the patient (the subject's speech serves as a command, and the device responds upon receiving a command).

The controller 114 can apply the processes and algorithms described herein with respect to FIGS. 3-8 to the sensor data to determine biometric parameters and other person-specific information for single or multiple subjects at rest and in motion. The classifier 119 can apply the processes and algorithms described herein with respect to FIGS. 3-8 to the sensor data to determine biometric parameters and other person-specific information for single or multiple subjects at rest and in motion. The classifier 119 can apply classifiers to the sensor data to determine the biometric parameters and other person-specific information via machine learning. In implementations, the classifier 119 may be implemented by the controller 114. In implementations, the sensor data and the biometric parameters and other person-specific information can be stored in the database 116. In implementations, the sensor data, the biometric parameters and other person-specific information, and/or combinations thereof can be transmitted or sent via the communication interface 118 to the computing platform 120 for processing, storage, and/or combinations thereof. The communication interface 118 can be any interface and use any communications protocol to communicate or transfer data between origin and destination endpoints. In an implementation, the device 110 can be any platform or structure which uses the one or more sensors 112 to collect the data from a subject(s) for use by the controller 114 and/or computing platform 120 as described herein. For example, the device 110 may be a combination of a substrate, frame, legs, and multiple load or other sensors 112 as described in FIG. 2. The device 110 and the elements therein may include other elements which may be desirable or necessary to implement the devices, systems, and methods described herein. However, because such elements and steps are well known in the art, and because they do not facilitate a better understanding of the disclosed embodiments, a discussion of such elements and steps may not be provided herein.

In implementations, the computing platform 120 can include a processor 122, a database 124, and a communication interface 126. In implementations, the computing platform 120 may include a classifier 129 for applicable and appropriate machine learning techniques as described herein. The processor 122 can obtain the sensor data from the sensors 112 or the controller 114 and can apply the processes and algorithms described herein with respect to FIGS. 3-8 to the sensor data to determine biometric parameters and other person-specific information for single or multiple subjects at rest and in motion. In implementations, the processor 122 can obtain the biometric parameters and other person-specific information from the controller 114 to store in database 124 for temporal and other types of analysis. In implementations, the classifier 129 can apply the processes and algorithms described herein with respect to FIGS. 3-8 to the sensor data to determine biometric parameters and other person-specific information for single or multiple subjects at rest and in motion. The classifier 129 can apply classifiers to the sensor data to determine the biometric parameters and other person-specific information via machine learning. In implementations, the classifier 129 may be implemented by the processor 122. In implementations, the sensor data and the biometric parameters and other person-specific information can be stored in the database 124. The communication interface 126 can be any interface and use any communications protocol to communicate or transfer data between origin and destination endpoints. In implementations, the computing platform 120 may be a cloud-based platform. In implementations, the processor 122 can be a cloud-based computer or off-site controller. In implementations, the processor 112 can be a single processor for both mechanical force sensors and audio sensors, or a set of processors to process mechanical force and interact with the speech capable device 150. The computing platform 120 and elements therein may include other elements which may be desirable or necessary to implement the devices, systems, and methods described herein. However, because such elements and steps are well known in the art, and because they do not facilitate a better understanding of the disclosed embodiments, a discussion of such elements and steps may not be provided herein.

In implementations, the machine learning training platform 430 can access and process sensor data to train and generate classifiers. The classifiers can be transmitted or sent to the classifier 129 or to the classifier 119.

In implementations, the SHMS 100 can interchangeably or additionally include the speech enabled device 150 as a bi-directional speech interface. In implementations, the speech enabled device 150 could replace the audio interface 111 or could work with the audio interface 111. The speech enabled device 150 can communicate with the device 100 and/or computing platform 120. In an implementation, the speech capable device 150 can be a voice assistant device (such as Alexa®, Siri®, and Google®) that communicates with the device 100 or the computing platform 120 through APIs. The speech enabled device 150 can act as a speech recognizer or speech synthesizer to support unidirectional and bi-directional communication with the subject.

FIGS. 2A-2J are illustrations of sensor placements and configurations. As described herein, the SHMS 100 can include one or more audio input sensors 200 such as microphones or acoustic sensors. The sensor placements and configurations shown in FIGS. 2A-2J are with respect to a bed 230 and surrounding environment. For example, U.S. patent application Ser. No. 16/595,848, filed Oct. 8, 2019, the entire disclosure of which is hereby incorporated by reference, describes example beds and environments applicable to the sensor placements and configurations described herein.

FIG. 2A shows an example of the one or more audio input sensors 200 inside a control box (controller) 240. FIG. 2B shows an example of the one or more audio input sensors 200 attached to a headboard 250 proximate the bed 230. FIG. 2C shows an example of the one or more audio input sensors 200 mounted to a wall 260 proximate the bed 230. FIG. 2D shows an example of the one or more audio input sensors 200 inside or attached to legs 270 of the bed 230. FIG. 2E shows an example of the one or more audio input sensors 200 integrated inside a force sensors box 280 under the legs 270 of the bed 230. FIG. 2F shows an example of the one or more audio input sensors 200 placed into or attached to a bed frame 290 of the bed 230.

In implementations, the SHMS 100 can include one or more speakers 210. FIG. 2G shows an example of the one or more speakers 210 inside the control box (controller) 240. FIG. 2F shows an example of the one or more speakers 210 placed into or attached to a bed frame 290 of the bed 230. FIG. 2H shows an example of the one or more speakers 210 integrated inside a force sensors box 280 under the legs 270 of the bed 230. FIG. 2I shows an example of the one or more speakers 210 mounted to a wall 260 proximate the bed 230. FIG. 2J shows an example of the one or more speakers 210 attached to a headboard 250 proximate the bed 230.

FIGS. 2A-2E and 2G are examples of systems with unidirectional audio communications and FIGS. 2F and 2H-2J are examples of systems with bidirectional audio communications.

Figure 3:
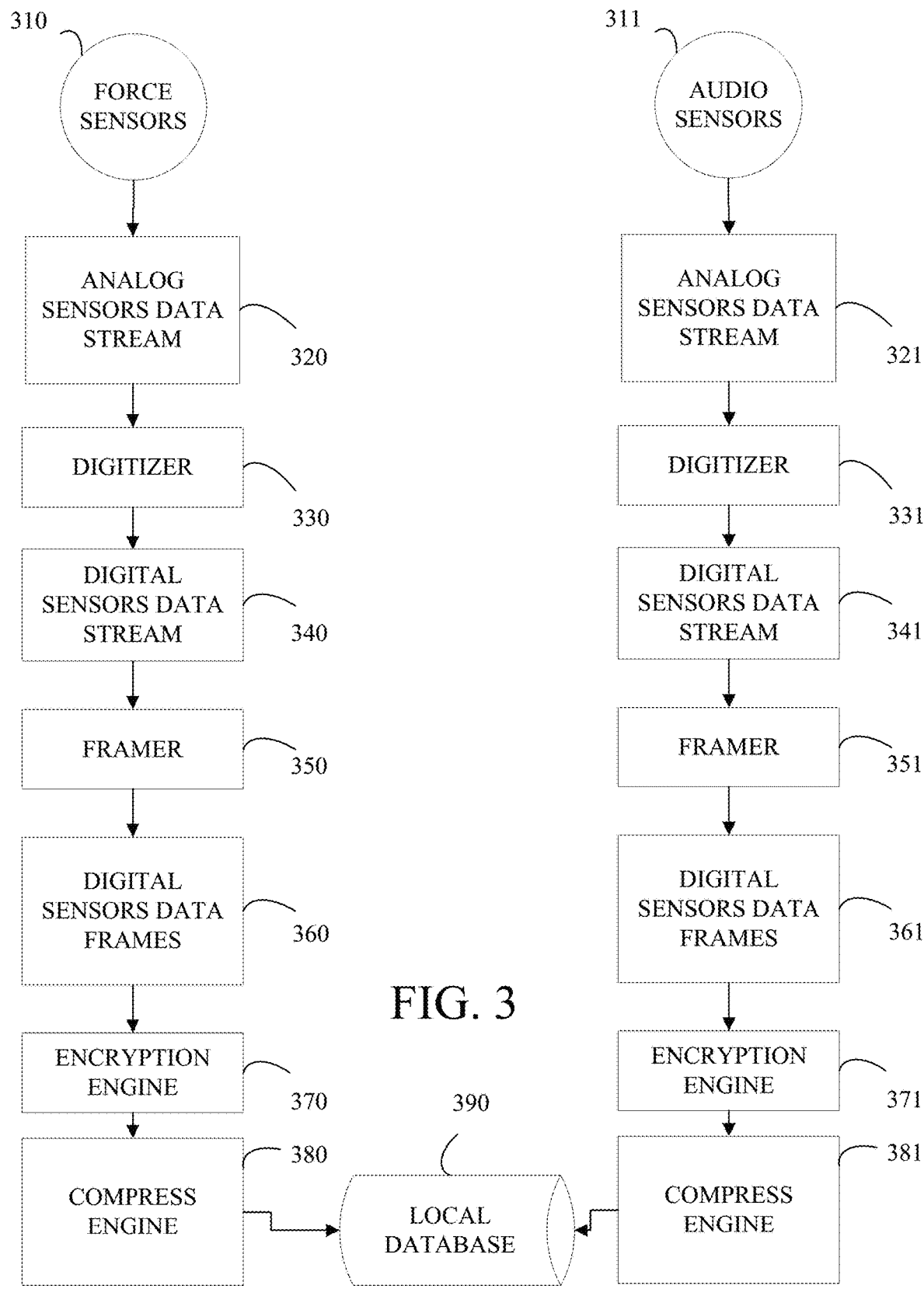
FIG. 3 is a processing pipeline for obtaining sensors data.

FIG. 3 is a processing pipeline 300 for obtaining sensor data such as, but not limited to, force sensor data, audio sensor data, and other sensor data, and processing the force sensor data, audio sensor data, and other sensor data.

An analog sensors data stream 320 is received from sensors 310. The sensors 310 can record mechanical force and vibrations of the body, including motion and physiological movements of heart and lungs using one or more non-contact sensors such as accelerometer, pressure, load, weight, force, motion or vibration sensors. A digitizer 330 digitizes the analog sensors data stream into a digital sensors data stream 340. A framer 350 generates digital sensors data frames 360 from the digital sensors data stream 340 which includes all the digital sensors data stream values within a fixed or adaptive time window. An encryption engine 370 encodes the digital sensors data frames 360 such that the data is protected from unauthorized access. A compression engine 380 compresses the encrypted data to reduce the size of the data that is going to be saved in the database 390. This reduces cost and provides faster access during read time. The database 390 can be local, offsite storage, cloud-based storage, or combinations thereof.

An analog sensors data stream 321 is received from sensors 311. The sensors 311 can record audio information including the subject's breathing and speech. A digitizer 331 digitizes the analog sensors data stream into a digital sensors data stream 341. A framer 351 generates digital sensors data frames 361 from the digital sensors data stream 341 which includes all the digital sensors data stream values within a fixed or adaptive time window. An encryption engine 371 encodes the digital sensors data frames 361 such that the data is protected from unauthorized access. In implementations, the encryption engine 371 can filter the digital audio sensors data frames 361 to a lower and narrower frequency band. In implementations, the encryption engine 371 can mask the digital audio sensors data frames 361 using a mask template. In implementations, the encryption engine 371 can transform the digital audio sensors data frames 361 using a mathematical formula. A compression engine 380 compresses the encrypted data to reduce the size of the data that is going to be saved in the database 390. This reduces cost and provides faster access during read time. The database 390 can be local, offsite storage, cloud-based storage, or combinations thereof.

The processing pipeline 300 shown in FIG. 3 is illustrative and can include any, all, none or a combination of the blocks or modules shown in FIG. 3. The processing order shown in FIG. 3 is illustrative and the processing order may vary without departing from the scope of the specification or claims.

Figure 4:
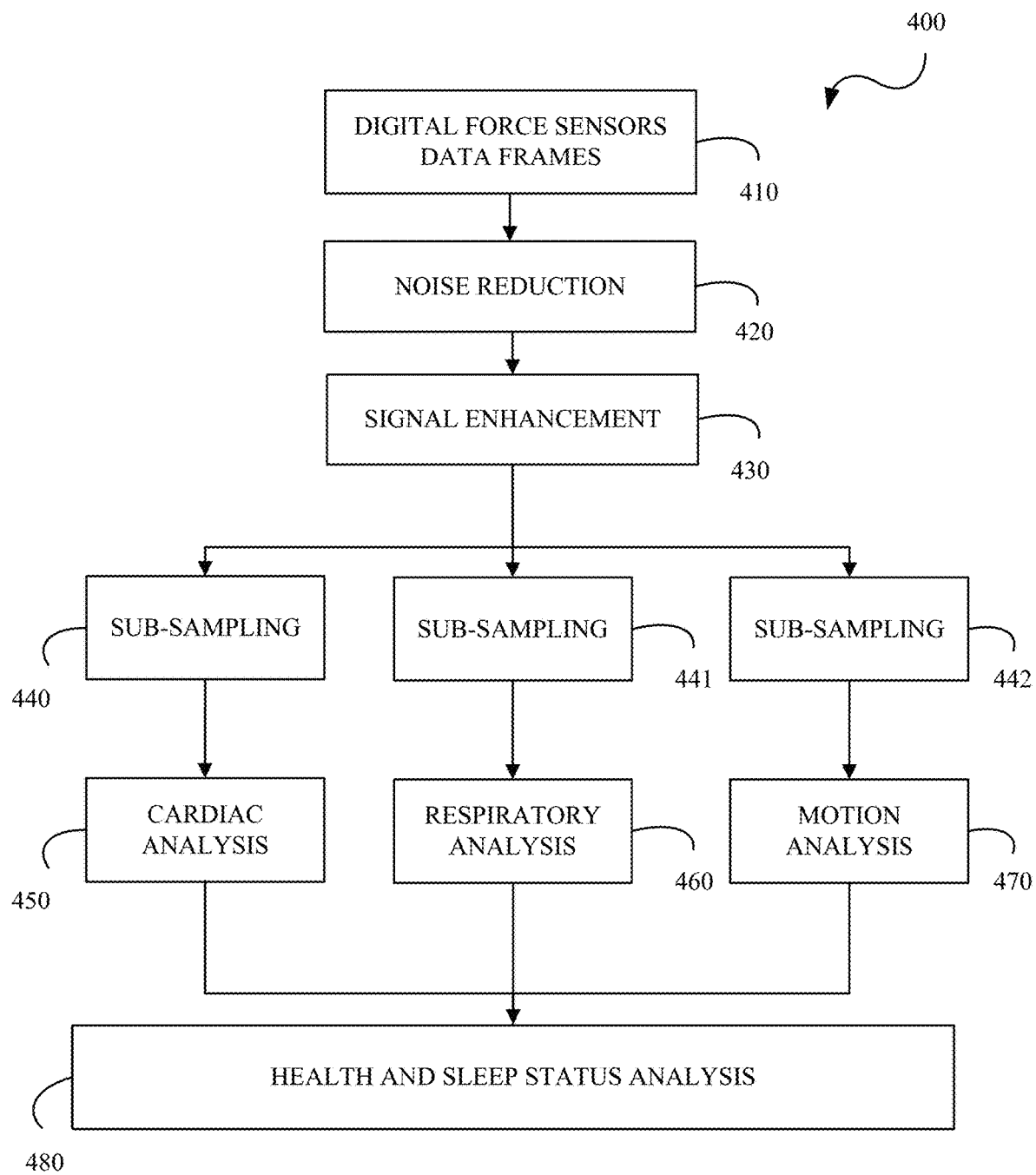
FIG. 4 is a processing pipeline for analyzing force sensors data.

FIG. 4 is a pre-processing pipeline 400 for processing the force sensor data. The pre-processing pipeline 400 processes digital force sensor data frames 410. A noise reduction unit 420 removes or attenuates noise sources that might have the same or different level of impact on each sensor. The noise reduction unit 420 can use a variety of techniques including, but not limited to, subtraction, combination of the input data frames, adaptive filtering, wavelet transform, independent component analysis, principal component analysis, and/or other linear or nonlinear transforms. A signal enhancement unit 430 can improve the signal to noise ratio of the input data. The signal enhancement unit 430 can be implemented as a linear or nonlinear combination of input data frames. For example, the signal enhancement unit 430 may combine the signal deltas to increase the signal strength for higher resolution algorithmic analysis. Subsampling units 440, 441 and 442 sample the digital enhanced sensor data and can include downsampling, upsampling, or resampling. The subsampling can be implemented as a multi-stage sampling or multi-phase sampling, and can use the same or different sampling rates for cardiac, respiratory and coughing analysis.

Cardiac analysis 450 determines the heart rate, heartbeat timing, variability, and heartbeat morphology and their corresponding changes from a baseline or a predefined range. An example process for cardiac analysis is shown in U.S. Provisional Application Patent Ser. No. 63/003,551, filed Apr. 1, 2020, the entire disclosure of which is hereby incorporated by reference. Respiratory analysis 460 determines the breathing rate, breathing phase, depth, timing and variability, and breathing morphology and their corresponding changes from a baseline or a predefined range. An example process for respiratory analysis is shown in U.S. Provisional Application Patent Ser. No. 63/003,551, filed Apr. 1, 2020, the entire disclosure of which is hereby incorporated by reference. Motion analysis 470 determines the movements amplitude, time, periodicity, and pattern and their corresponding changes from a baseline or a predefined range. Health and sleep status analysis 480 combines the data from cardiac analysis 450, respiratory analysis 460 and motion analysis 470 to determine the subject's health status, sleep quality, out-of-the norm events, diseases and conditions.

The processing pipeline 400 shown in FIG. 4 is illustrative and can include any, all, none or a combination of the blocks or modules shown in FIG. 4. The processing order shown in FIG. 4 is illustrative and the processing order may vary without departing from the scope of the specification or claims.

Figure 5:
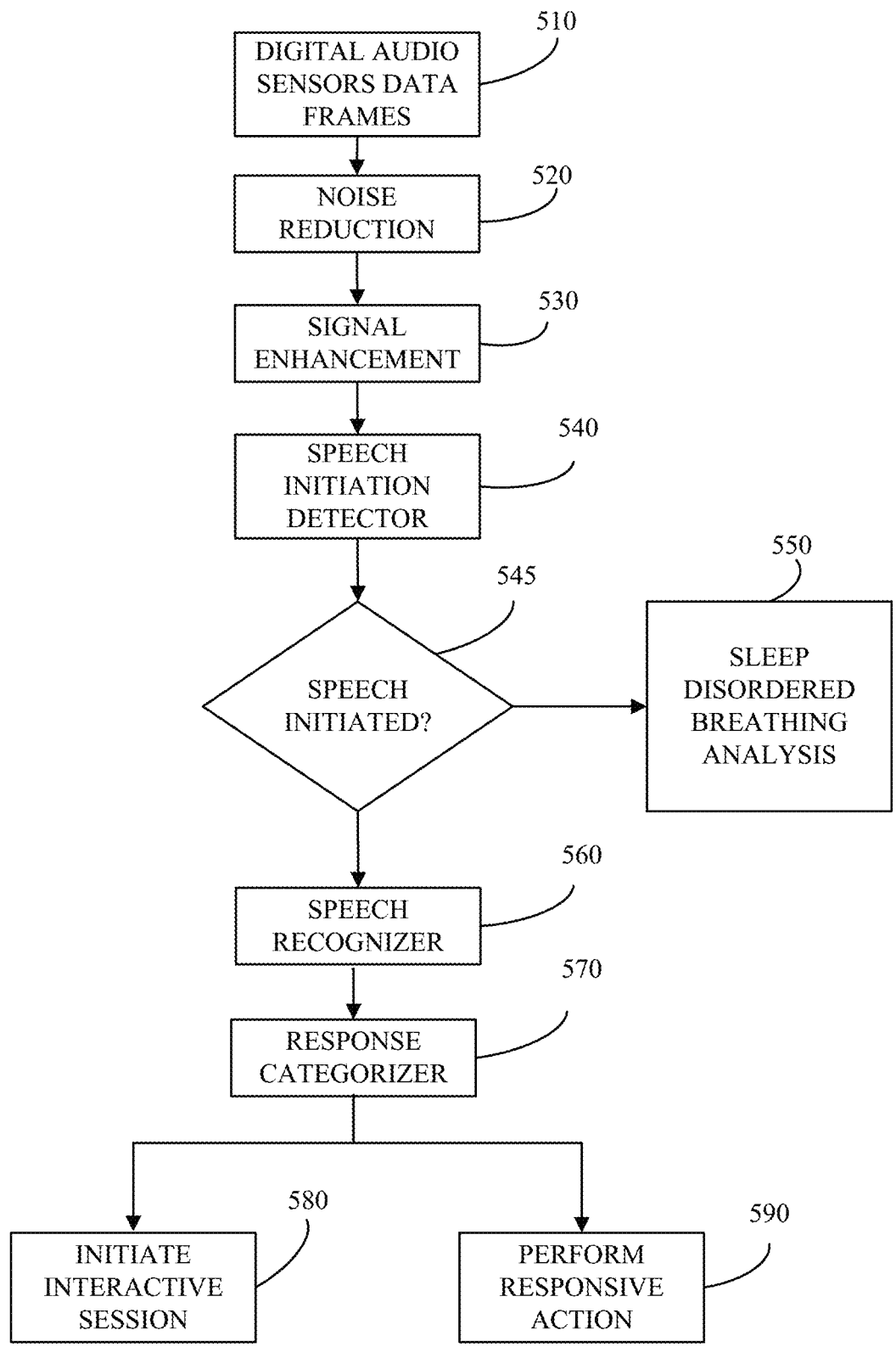
FIG. 5 is a processing pipeline for analyzing audio sensors data from audio sensors.

FIG. 5 is an example process 500 for analyzing the audio sensor data. The pipeline 500 processes digital audio sensor data frames 510. A noise reduction unit 520 removes or attenuates environmental or other noise sources that might have the same or different level of impact on each sensor. The noise reduction unit 520 can use a variety of techniques including, but not limited to, subtraction, combination of the input data frames, adaptive filtering, wavelet transform, independent component analysis, principal component analysis, and/or other linear or nonlinear transforms. A signal enhancement unit 530 can improve the signal to noise ratio of the input data. Speech initiation detector 540 determines if the subject is verbally communicating with the system. The detector 540 compares the audio stream against a dictionary of electronic commands to discard unrelated conversations and determines 545 if a verbal command to interact has been initiated.

If no verbal command has been initiated, the enhanced digital audio sensor data frames will be analyzed using sleep disordered breathing analyzer 550 to detect breathing disturbances. Sleep disordered breathing analyzer 550 uses digital audio sensors data frames 510, digital force sensors data frames 410, or both to determine breathing disturbances. The sleep disordered breathing analyzer 550 uses envelope detection algorithms, time domain, spectral domain, or time frequency domain analysis to identify the presence, intensity, magnitude, duration and type of sleep disordered breathing.

If it is determined that a verbal command has been initiated, the speech recognizer 560 processes the enhanced digital audio sensor data frames to identify the context of speech. In implementations, the speech recognizer 560 includes an electronic command recognizer that compares the subject's speech against a dictionary of electronic commands. In implementations, the speech recognizer uses artificial intelligence algorithms to identify speech. In implementations, the speech recognizer 560 uses a speech to text engine to translate the subject's verbal commands into strings of text. Response categorizer 570 processes the output from the speech recognizer and determines if an interactive session 580 should be initiated or a responsive action 590 should be performed. Examples of an interactive session are playing back a tone or playing a synthesized speech. Examples of a responsive action are turning on/off a home automation feature, labeling the data with health status markers for future access of the subject or subject's physician, calling emergency services, or interacting with another speech capable device.

The processing pipeline 500 shown in FIG. 5 is illustrative and can include any, all, none or a combination of the components, blocks or modules shown in FIG. 5. The processing order shown in FIG. 5 is illustrative and the processing order may vary without departing from the scope of the specification or claims.

Figure 6:
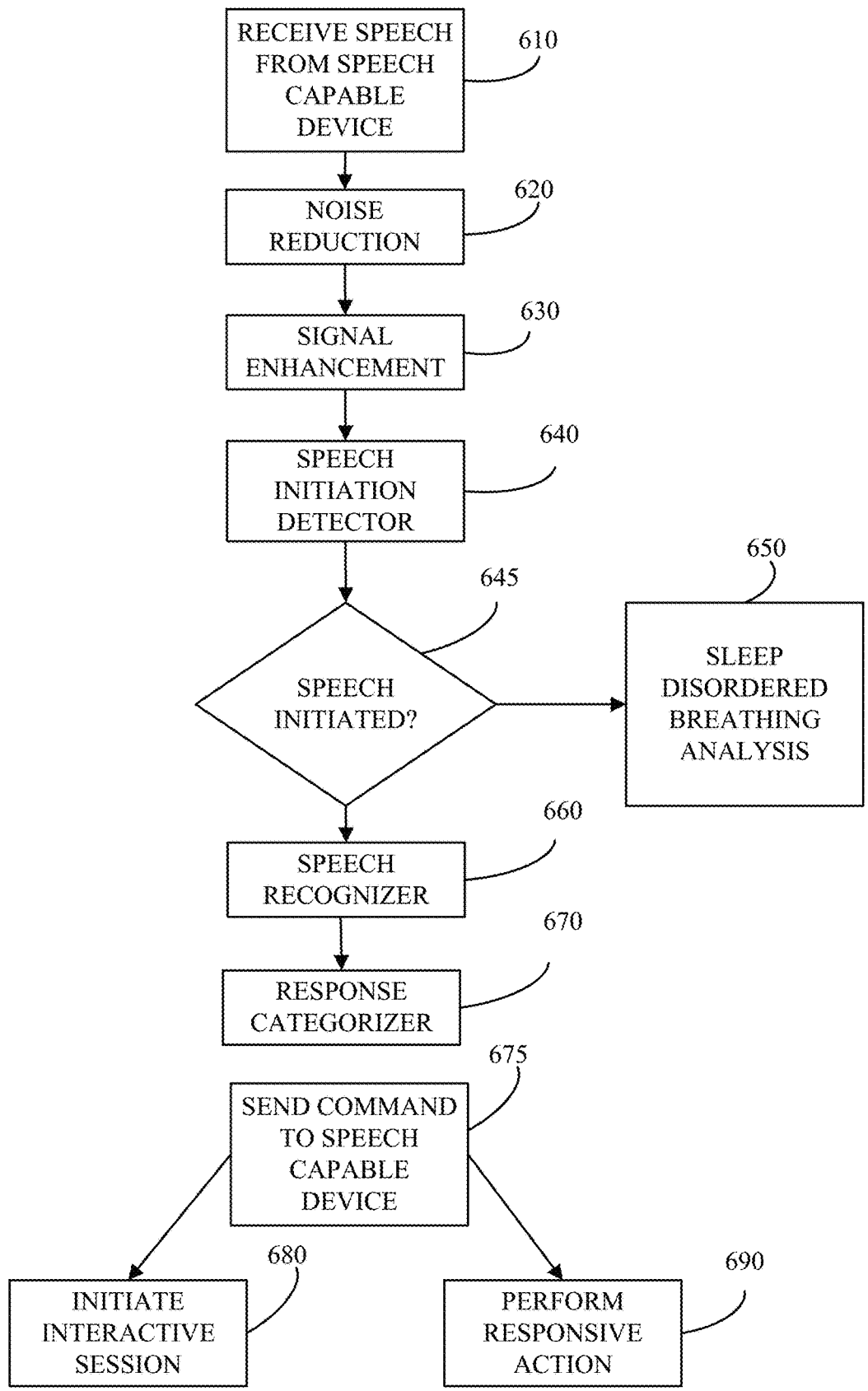
FIG. 6 is a processing pipeline for analyzing audio sensors data using a speech capable device.

FIG. 6 is an example process 600 for analyzing the audio sensor data by interacting with a speech capable device. In implementations, the speech capable device can be a voice assistant device (such as Alexa®, Siri®, and Google®) acting as a speech recognizer that communicates through APIs.

The pipeline 600 receives speech data 610 from the speech capable device. A noise reduction unit 620 removes or attenuates environmental or other noise sources that might have the same or different level of impact on the speech data. The noise reduction unit 620 can use a variety of techniques including, but not limited to, subtraction, combination of the input data frames, adaptive filtering, wavelet transform, independent component analysis, principal component analysis, and/or other linear or nonlinear transforms. A signal enhancement unit 530 can improve the signal to noise ratio of the speech data. Speech initiation detector 640 determines if the subject is verbally communicating with the system. The detector 640 compares the speech data against a dictionary of electronic commands to discard unrelated conversations and determines 645 if a verbal command to interact has been initiated.

If no verbal command has been initiated, the enhanced digital speech data frames will be analyzed using sleep disordered breathing analyzer 650 to detect breathing disturbances. Sleep disordered breathing analyzer 650 uses speech data 610, digital force sensors data frames 410, or both to determine breathing disturbances. The sleep disordered breathing analyzer 650 uses envelope detection algorithms, time domain, spectral domain, or time frequency domain analysis to identify the presence, intensity, magnitude, duration and type of sleep disordered breathing.

If it is determined that a verbal command has been initiated, the speech recognizer 660 processes the speech data frames to identify the context of speech. In implementations, the speech recognizer 660 includes an electronic command recognizer that compares the subject's speech against a dictionary of electronic commands. In implementations, the speech recognizer uses artificial intelligence algorithms to identify speech. In implementations, the speech recognizer 660 uses a speech to text engine to translate the subject's verbal commands into strings of text. Response categorizer 670 processes the output from the speech recognizer and determines if an interactive session 680 should be initiated or a responsive action 690 should be performed. Commands corresponding to the categorized response are sent 675 to the speech capable device through APIs. In implementations, the speech enabled device can act as a speech synthesizer to initiate interactive session 680. In implementations, the speech enabled device can also connect to home automation systems or notification systems to perform responsive action 690. Examples of an interactive session are playing back a tone or playing a synthesized speech. Examples of a responsive action are turning on/off a home automation feature, labeling the data with health status markers for future access of the subject or subject's physician, calling emergency services, or interacting with another speech capable device.

The processing pipeline 600 shown in FIG. 6 is illustrative and can include any, all, none or a combination of the components, blocks or modules shown in FIG. 6. The processing order shown in FIG. 6 is illustrative and the processing order may vary without departing from the scope of the specification or claims.

Figure 7:
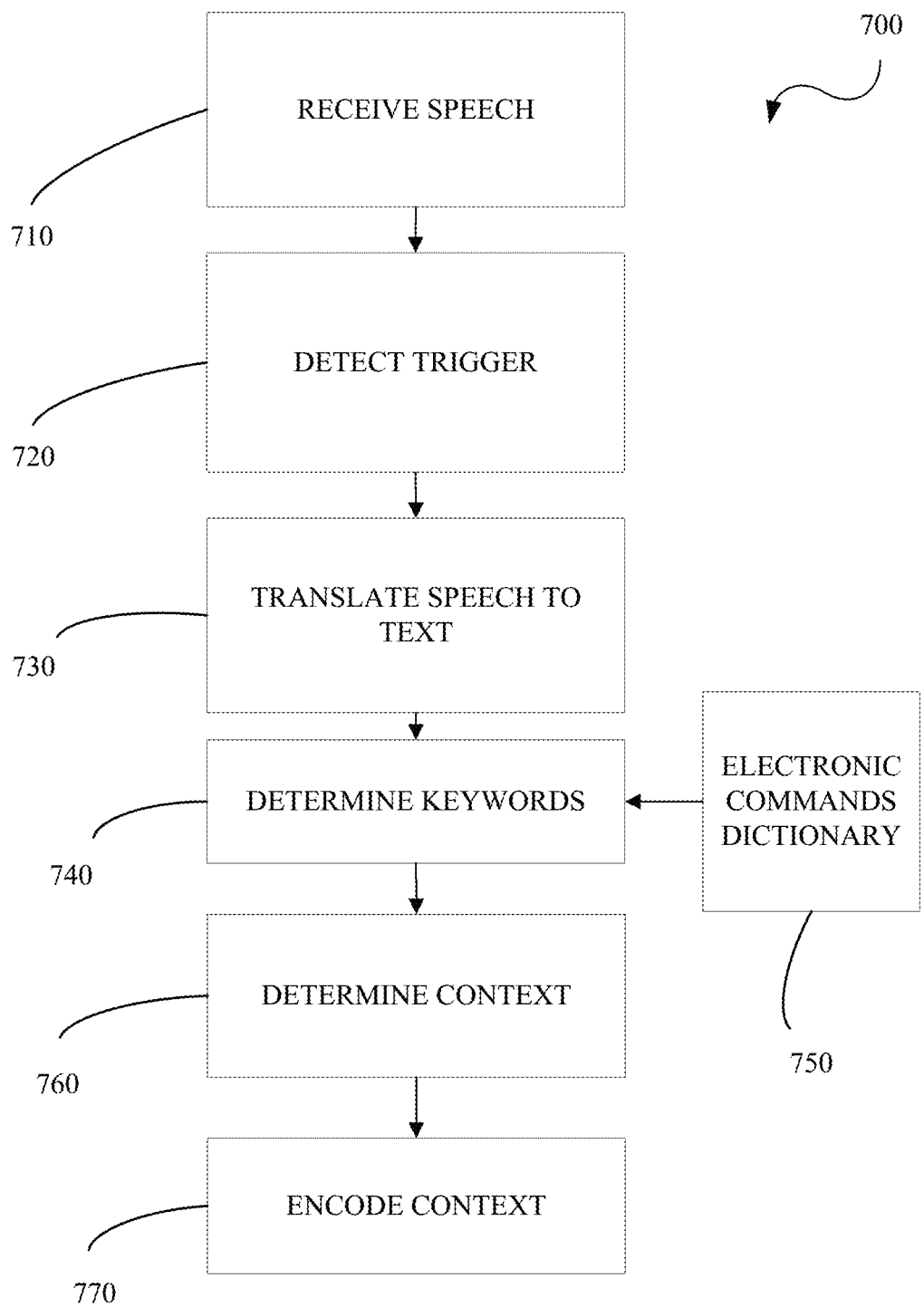
FIG. 7 is a processing pipeline for recognizing speech.

FIG. 7 is an example process 700 for recognizing speech by a speech recognizer. The speech recognizer receives 710 the enhanced audio data streams after it is determined that speech has been initiated as described in FIG. 5. The speech recognizer detects 720 parts of the electronic command that match a specific request through speech processing, i.e., detects a trigger. The speech recognizer translates 730 the speech into text. The speech recognizer matches 740 the strings of text against a dictionary of electronic commands 750. The speech recognizer determines 760 the context of the speech. A context is the general category of the subject's verbal request. Examples are running a health check, labeling or annotating the data for a health relate episode, communication with the subject's physician, communication with the emergency services, ordering a product, and interacting with home automation. The speech recognizer encodes 770 the context and prepares it for the response categorizer 570.

The processing pipeline 700 shown in FIG. 7 is illustrative and can include any, all, none or a combination of the components, blocks or modules shown in FIG. 7. The processing order shown in FIG. 7 is illustrative and the processing order may vary without departing from the scope of the specification or claims.

Figure 8:
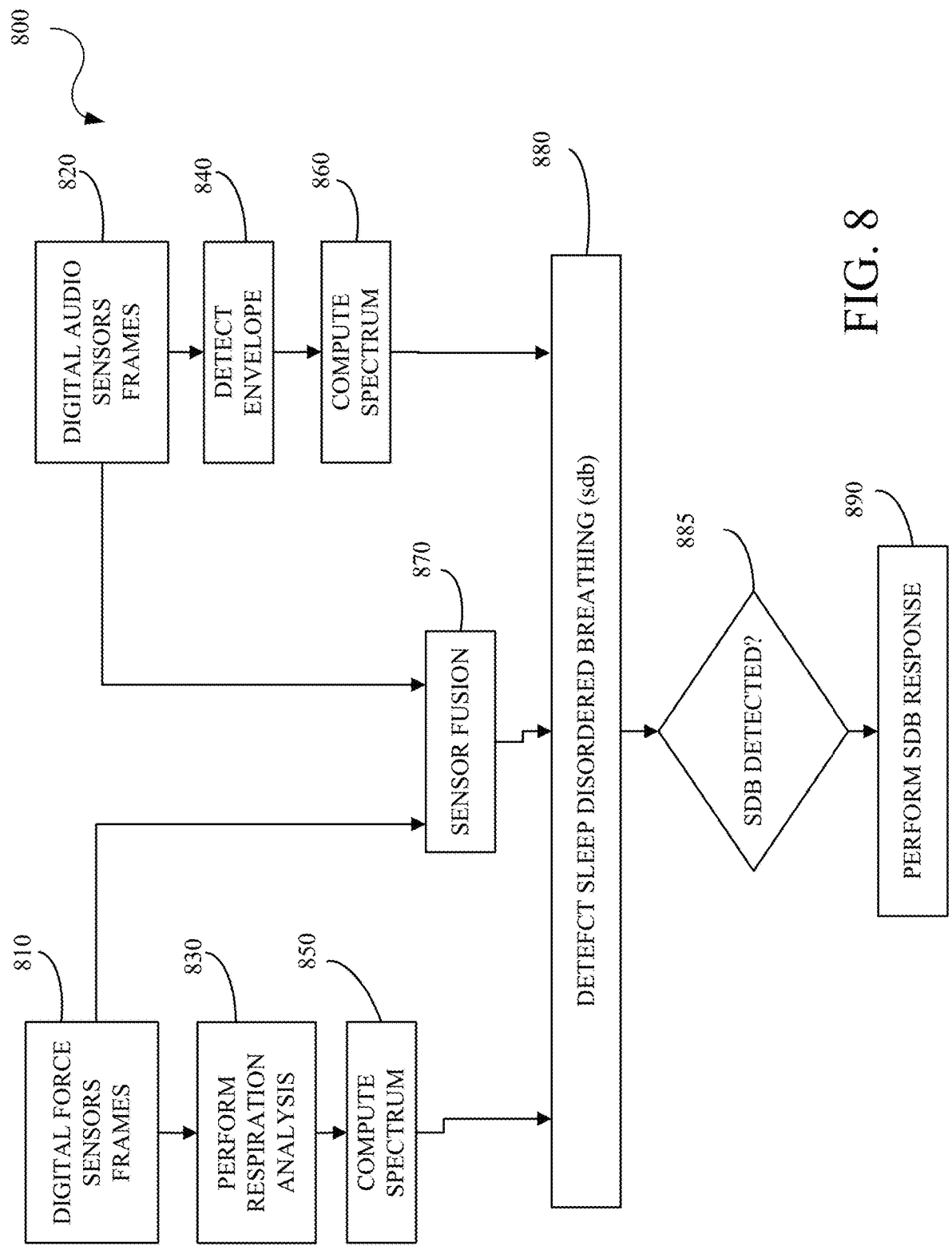
FIG. 8 is a processing pipeline for sleep disordered breathing (SDB) detection and response.

FIG. 8 is an example process 800 for sleep disordered breathing (SDB) detection and response. Digital force sensors frames 810 are received as processed in FIG. 3 and FIG. 4. A respiration analysis 830 is performed on the digital force sensors frames 810. The respiration analysis 830 can include filtering, combining, envelope detection, and other algorithms. A spectrum or time frequency spectrum is computed 850 on the output of the respiration analysis 830. Digital audio force sensors frames 820 are received as processed in FIG. 3 and FIG. 5. Envelope detection 840 is performed on the digital audio force sensors frames 820. A spectrum or time frequency spectrum is computed 860 on the output of the envelope detection 840. Fused sensor processing 870 is performed on the digital force sensors frames 810 and the digital audio sensors frames 820 such as normalized amplitude or frequency parameters, cross correlation, or coherence or similar metrics of similarity to create combined signals or feature sets.

Sleep disordered breathing (SDB) is determined 880 using the envelope, time domain, frequency domain, time-frequency and parameters from the fusion of force and audio sensors. Implementations include threshold based techniques, template matching methods, or use of classifiers to detect sleep disordered breathing. Once sleep disordered breathing is detected, process 880 determines the intensity (for example, light, mild, moderate, severe), magnitude, duration and type of sleep disordered breathing. If sleep disordered breathing is detected 885, a proper response 890 is determined for the detected SDB such as changing an adjustable feature of the bed (for example, firmness), bedroom (for example, lighting), play a sound to make the sleeper change position, or transition into a lighter state of sleep and therefore, help stop, reduce or alter the disordered breathing.

The processing pipeline 800 shown in FIG. 8 is illustrative and can include any, all, none or a combination of the components, blocks or modules shown in FIG. 8. The processing order shown in FIG. 8 is illustrative and the processing order may vary without departing from the scope of the specification or claims.

FIG. 7 is a flowchart of a method 700 for determining weight from the MSMDA data. The method 700 includes: obtaining 710 the MSMDA data; calibrating 720 the MSMDA data; performing 730 superposition analysis on the calibrated MSMDA data; transforming 740 the MSMDA data to weight; finalizing 750 the weight; and outputting 760 the weight.

The method 700 includes obtaining 710 the MSMDA data. The MSMDA data is generated from the pre-processing pipeline 600 as described.

The method 700 includes calibrating 720 the MSMDA data. The calibration process compares the multiple sensors readings against an expected value or range. If the values are different, the MSMDA data is adjusted to calibrate to the expected value range. Calibration is implemented by turning off all other sources (i.e. set them to zero) in order to determine the weight of the new object. For example, the weight of the bed, bedding and pillow are determined prior to the new object. A baseline is established of the device, for example, prior to use. In an implementation, once a subject or object (collectively "item") is on the device, an item baseline is determined and saved. This is done so that data from a device having multiple items can be correctly processed using the methods described herein.

The method 700 includes performing 730 superposition analysis on the calibrated MSMDA data. Superposition analysis provides the sum of the readings caused by each independent sensor acting alone. The superposition analysis can be implemented as an algebraic sum, a weighted sum, or a nonlinear sum of the responses from all the sensors.

The method 700 includes transforming 740 the MSMDA data to weight. A variety of known or to be known techniques can be used to transform the sensor data, i.e. the MSMDA data, to weight.

The method 700 includes finalizing 750 the weight. In an implementation, finalizing the weight can include smoothing, checking against a range, checking against a dictionary, or a past value. In an implementation, finalizing the weight can include adjustments due to other factors such as bed type, bed size, location of the sleeper, position of the sleeper, orientation of the sleeper, and the like.

The method 700 includes and outputting 760 the weight. The weight is stored for use in the methods described herein.

Implementations of controller 200, controller 214, processor 422, and/or controller 414 (and the algorithms, methods, instructions, etc., stored thereon and/or executed thereby) can be realized in hardware, software, or any combination thereof. The hardware can include, for example, computers, intellectual property (IP) cores, application-specific integrated circuits (ASICs), programmable logic arrays, optical processors, programmable logic controllers, microcode, microcontrollers, servers, microprocessors, digital signal processors or any other suitable circuit. In the claims, the term "controller" should be understood as encompassing any of the foregoing hardware, either singly or in combination.

Further, in one aspect, for example, controller 200, controller 214, processor 422, and/or controller 414 can be implemented using a general purpose computer or general purpose processor with a computer program that, when executed, carries out any of the respective methods, algorithms and/or instructions described herein. In addition or alternatively, for example, a special purpose computer/processor can be utilized which can contain other hardware for carrying out any of the methods, algorithms, or instructions described herein.

Controller 200, controller 214, processor 422, and/or controller 414 can be one or multiple special purpose processors, digital signal processors, microprocessors, controllers, microcontrollers, application processors, central processing units (CPU)s, graphics processing units (GPU)s, digital signal processors (DSP)s, application specific integrated circuits (ASIC)s, field programmable gate arrays, any other type or combination of integrated circuits, state machines, or any combination thereof in a distributed, centralized, cloud-based architecture, and/or combinations thereof.

In general, a device includes a substrate configured to support a subject, a plurality of non-contact sensors configured to capture acoustic signals and force signals with respect to the subject, an audio interface configured to communicate with the subject, and a processor in connection with the plurality of sensors and the audio interface. The processor configured to determine biosignals from one or more of the acoustic signals and the force signals to monitor a subject's health status, and detect presence of speech in the acoustic signals. The audio interface configured to interactively communicate with at least one of the subject or an entity associated with the subject based on at least one of an action needed due to the subject's health status and a verbal command in detected speech.

In implementations, the processor further configured to encrypt digitized acoustic signals by at least one of filter the digitized acoustic signals to a lower and narrower frequency, mask the digitized acoustic signals using a mask template or an encryption key, and transform the digitized acoustic signals using a mathematical formula. In implementations, the processor further configured to compare the acoustic signals against a dictionary of electronic commands to discard unrelated conversations, determine the presence of the verbal command, identify a context of speech upon determination of the verbal command, and perform at least one of: initiate an interactive session, via the audio interface, with the at least one of the subject or another entity based on the verbal command and the context of speech, and determine a responsive action based on the verbal command and the context of speech. In implementations, the audio interface is further configured to recognize and respond to voice commands from designated individuals. In implementations, the processor further configured to: compare the acoustic signals against a dictionary of electronic commands to discard unrelated conversations, determine the presence of the verbal command; analyze the acoustic signals to detect breathing disturbances upon failure to detect the verbal command, and determine a responsive action to detection of sleep disordered breathing (SDB). In implementations, the plurality of non-contact sensors configured to capture force signals from subject actions with respect to the substrate, the processor further configured to perform at least one of cardiac analysis, respiratory analysis, and motion analysis based on the force signals to determine the subject's health status. In implementations, when performing breathing disturbances analysis to determine the subject's health status, the processor further configured to: fuse the force signals and the acoustic signals based on one or more similarity metrics to generate fusion signals, detect sleep disordered breathing (SDB) using the fusion signals, the force signals, and the acoustic signals, and determine a responsive action to detection of the SDB. In implementations, wherein the responsive action is one or more of: an audible tone, an audible message, a trigger for a home automation device, a trigger for a speech assistant device, a call to an entity or emergency services, marking data for future access, a database entry, and a health check-up. In implementations, the processor further configured to determine an intensity, magnitude, duration, and type of the SDB.

In general, a system includes a speech capable device configured to communicate with at least one of a subject or an entity associated with the subject, and a device in communication with the speech capable device, The device including a substrate configured to support the subject, a plurality of non-contact sensors configured to capture acoustic signals with respect to the subject and force signals from subject actions with respect to the substrate, and a processor in connection with the plurality of sensors and the audio interface. The processor configured to: monitor a subject's health status based on the force signals and the acoustic signals, and detect a verbal command in the acoustic signals. The speech capable device configured to interactively communicate with at least the subject or the entity based on at least one of a responsive action needed due to the subject's health status and detection of the verbal command.

In implementations, the processor further configured to encrypt digitized acoustic signals by at least one of filter the digitized acoustic signals to a lower and narrower frequency, mask the digitized acoustic signals using a mask template or an encryption key, and transform the digitized acoustic signals using a mathematical formula. In implementations, the processor further configured to compare the acoustic signals against a dictionary of electronic commands to discard unrelated conversations, determine the presence of the verbal command, identify a context of speech upon determination of the verbal command, and perform at least one of: initiate an interactive session, via the speech capable device, with the at least one of the subject or the entity based on the verbal command and the context of speech, and determine the responsive action based on the verbal command and the context of speech. In implementations, the speech capable device is further configured to recognize and respond to voice commands from designated individuals. In implementations, the processor further configured to perform at least respiratory analysis based on the force signals, compare the acoustic signals against a dictionary of electronic commands to discard unrelated conversations, determine the presence of the verbal command, fuse the force signals and the acoustic signals based on one or more similarity metrics to generated fusion signals upon failure to detect the verbal command, detect sleep disordered breathing (SDB) using the fusion signals, the force signals, and the acoustic signals, and determine a responsive action to detection of the SDB. In implementations, the processor further configured to determine an intensity, magnitude, duration, and type of the SDB. In implementations, the responsive action is one or more of: an audible tone, an audible message, a trigger for a home automation device, a trigger for a speech assistant device, a call to an entity or emergency services, marking data for future access, a database entry, and a health check-up.

In general, a method for determining item specific parameters includes capturing audio signals and force signals from a plurality of non-contact sensors placed relative to a subject on a substrate, determining at least biosignal information from the audio signals and the force signals, detecting a presence of speech in the acoustic signals, and interactively communicating with at least one of the subject or an entity associated with the subject based on at least one of an action needed due to a subject's health status and a verbal command found in detected speech.

In implementations, the method further includes encrypting digitized acoustic signals by at least one of filter the digitized acoustic signals to a lower and narrower frequency, mask the digitized acoustic signals using a mask template or an encryption key, and transform the digitized acoustic signals using a mathematical formula. In implementations, the method further includes comparing the acoustic signals against a dictionary of electronic commands to discard unrelated conversations, determining the presence of the verbal command, identifying a context of speech upon determination of the verbal command, and performing at least one of: initiating an interactive session, via the audio interface, with the at least one of the subject or another entity based on the verbal command and the context of speech, and determining a responsive action based on the verbal command and the context of speech. In implementations, the method further includes recognizing and responding to voice commands from designated individuals. In implementations, the method further includes comparing the acoustic signals against a dictionary of electronic commands to discard unrelated conversations, determining the presence of the verbal command, analyzing the acoustic signals to detect breathing disturbances upon failure to detect the verbal command, and determining a responsive action to detection of sleep disordered breathing (SDB). In implementations, the method further includes performing at least one of cardiac analysis, respiratory analysis, and motion analysis based on the force signals to determine the subject's health status. In implementations, the method further includes performing breathing disturbances analysis to determine the subject's health status, the performing further includes fusing the force signals and the acoustic signals based on one or more similarity metrics to generate fusion signals, detecting sleep disordered breathing (SDB) using the fusion signals, the force signals, and the acoustic signals, and determining a responsive action to detection of the SDB. In implementations, the responsive action is one or more of: an audible tone, an audible message, a trigger for a home automation device, a trigger for a speech assistant device, a call to an entity or emergency services, marking data for future access, a database entry, and a health check-up. In implementations, the method further includes determining an intensity, magnitude, duration, and type of the SDB. In implementations, the method further includes performing at least respiratory analysis based on captured force signals, comparing the acoustic signals against a dictionary of electronic commands to discard unrelated conversations, determining the presence of the verbal command, fusing the force signals and the acoustic signals based on one or more similarity metrics to generated fusion signals upon failure to detect the verbal command, detecting sleep disordered breathing (SDB) using the fusion signals, the force signals, and the acoustic signals, and determining a responsive action to detection of the SDB.

In general, a device includes a substrate configured to support a subject, a plurality of non-contact sensors configured to capture force signals with respect to the subject, a processor in connection with the plurality of sensors, the processor configured to determine biosignals from the force signals to monitor a subject's health status, and an audio interface configured to interactively communicate with at least one of the subject or an entity associated with the subject based on at least one of an action needed due to the subject's health status and a verbal command received via a speech capable device.

In general, a device includes a substrate configured to support a subject, a plurality of non-contact sensors configured to capture acoustic signals and force signals with respect to the subject, an audio interface configured to communicate with the subject, and a processor in connection with the plurality of sensors and the audio interface. The processor configured to determine biosignals from one or more of the acoustic signals and the force signals to monitor a subject's health status, and receive, from a speech detection entity, speech detected in the acoustic signals. The audio interface configured to interactively communicate with at least one of the subject or an entity associated with the subject based on at least one of an action needed due to the subject's health status and a verbal command in detected speech.

The word "example," "aspect," or "embodiment" is used herein to mean serving as an example, instance, or illustration. Any aspect or design described herein as using one or more of these words is not necessarily to be construed as preferred or advantageous over other aspects or designs. Rather, use of the word "example," "aspect," or "embodiment" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A device comprising:
a substrate configured to support a subject;
a plurality of non-contact sensors configured to capture acoustic signals and second signals with respect to the subject;
an audio interface; and
a processor in communication with the plurality of sensors and the audio interface, the processor configured to:
determine one or more biosignals from one or more of (i) the acoustic signals or (ii) the second signals to monitor a health status of the subject;
detect presence of speech in the acoustic signals; and
detect a verbal command in the speech,
wherein, in response to not detecting presence of the verbal command, the processor is configured to perform a sleep disordered breathing (SDB) analysis.

2. The device of claim 1, wherein the processor is further configured to: digitize the acoustic signals to obtain digitized acoustic signals, and encrypt the digitized acoustic signals by at least one of: filtering the digitized acoustic signals to a lower and narrower frequency than a frequency of the digitized acoustic signals, masking the digitized acoustic signals using a mask template or an encryption key, and transforming the digitized acoustic signals using a mathematical formula.

3. The device of claim 1, wherein the processor is further configured to:
identify a context of the speech upon detection of the verbal command; and
perform at least one of:
initiate an interactive session, via the audio interface, with the subject or an entity associated with the subject based on the verbal command and the context of the speech; and
determine a responsive action based on the verbal command and the context of the speech.

4. The device of claim 1, wherein the audio interface is further configured to recognize and respond to the verbal command from a designated individual.

5. The device of claim 1, wherein the processor is further configured to:
compare the acoustic signals against a dictionary of electronic commands to identify unrelated conversations to discard.

6. The device of claim 1, wherein the plurality of non-contact sensors are configured to capture second signals from an action of the subject with respect to the substrate, and the processor is further configured to perform at least one of cardiac analysis, respiratory analysis, and motion analysis based on the second signals to monitor the health status of the subject.

7. The device of claim 6, wherein the SDB analysis comprises breathing disturbances analysis, and wherein, when performing the breathing disturbances analysis to monitor the health status of the subject, the processor is further configured to:
fuse the second signals and the acoustic signals based on one or more similarity metrics to generate fusion signals;
detect the SDB using at least one of: (iii) the fusion signals, (iv) the second signals, or (v) the acoustic signals; and
determine a responsive action to detection of the SDB.

8. The device of claim 7, wherein the responsive action is one or more of:
an audible tone;
an audible message;
a trigger for a home automation device;
a trigger for a speech assistant device;
a call to an entity or emergency services;
marking data for future access;
a database entry; and
a health check.

9. The device of claim 7, wherein the processor is further configured to determine an intensity, magnitude, duration, and type of the SDB.

10. The device of claim 1, wherein, in response to detecting the presence of the verbal command, the audio interface is configured to interactively communicate with at least one of the subject or an entity associated with the subject based on at least one of an action needed due to the health status of the subject and the verbal command.

11. A system comprising:
a speech capable device configured to communicate with at least one of a subject or an entity associated with the subject;
an apparatus in communication with the speech capable device, the apparatus comprising:
a substrate configured to support the subject;
a plurality of non-contact sensors configured to capture acoustic signals with respect to the subject and second signals from subject actions with respect to the substrate;
a processor in connection with the plurality of non-contact sensors, the processor configured to:
monitor a health status of the subject based on one or more of (i) the second signals; or (ii) the acoustic signals;
detect presence of speech in the acoustic signals; and
detect a verbal command in the speech, wherein, in response to not detecting presence of the verbal command, the speech capable device is configured to perform a sleep disordered breathing (SDB) analysis.

12. The system of claim 11, wherein the processor is further configured to: digitize the acoustic signals to obtain digitized acoustic signals, and encrypt the digitized acoustic signals by at least one of: filtering the digitized acoustic signals to a lower and narrower frequency than a frequency of the digitized acoustic signals, masking the digitized acoustic signals using a mask template or an encryption key, and transforming the digitized acoustic signals using a mathematical formula.

13. The system of claim 11, wherein the processor is further configured to:
compare the acoustic signals against a dictionary of electronic commands to identify unrelated conversations to discard;
determine the presence of the verbal command;
identify a context of the speech upon detection of the verbal command; and
perform at least one of:
initiate an interactive session, via the speech capable device, with the at least one of the subject or the entity based on the verbal command and the context of the speech; and
determine a responsive action based on the verbal command and the context of the speech.

14. The system of claim 11, wherein the speech capable device is further configured to recognize and respond to the verbal command from a designated individual.

15. The system of claim 11, wherein the processor is further configured to:
perform respiratory analysis based on the second signals;
compare the acoustic signals against a dictionary of electronic commands to identify unrelated conversations to discard;
fuse the second signals and the acoustic signals based on one or more similarity metrics to generated fusion signals in response to not detecting the presence of the verbal command;
detect the SDB using at least one of: (iii) the fusion signals, (iv) the second signals, or (v) the acoustic signals; and
determine a responsive action to detection of the SDB.

16. The system of claim 15, wherein the processor is further configured to determine an intensity, magnitude, duration, and type of the SDB.

17. The system of claim 15, wherein the responsive action is one or more of:
an audible tone;
an audible message;
a trigger for a home automation device;
a trigger for a speech assistant device;

a call to an entity or emergency services;
marking data for future access;
a database entry; and
a health check.

18. A device comprising:
a substrate configured to support a subject;
a plurality of non-contact sensors configured to capture signals with respect to the subject;
a processor in connection with the plurality of sensors, the processor configured to:
  determine biosignals from the signals to monitor a health status of the subject;
  detect presence of speech in an acoustic signal; and
  detect a verbal command in the speech, wherein, in response to not detecting presence of the verbal command, the processor is configured to perform a sleep disordered breathing (SDB) analysis.

* * * * *